(12) United States Patent
Tsimerman

(10) Patent No.: US 6,193,510 B1
(45) Date of Patent: Feb. 27, 2001

(54) MEDICAL DEVICE WITH TIME-OUT FEATURE

(76) Inventor: Efraim Tsimerman, 480 Queens Quay West, Apt. 903W, Toronto, Ontario (CA), M5V 2Y5

( * ) Notice: Subject to any disclaimer, the term of this patent is extended or adjusted under 35 U.S.C. 154(b) by 0 days.

(21) Appl. No.: 09/361,979

(22) Filed: Jul. 28, 1999

(51) Int. Cl.7 .............................. A61C 1/00; A61C 3/00
(52) U.S. Cl. ............................................. 433/29; 433/27
(58) Field of Search ........................... 433/29, 215, 229, 433/27

(56) References Cited

U.S. PATENT DOCUMENTS 4,835,372 * 5/1989 Gombrich et al. .................... 235/375
5,715,831 * 2/1998 Johnson ................................. 600/539
6,113,549 * 9/2000 Johnson ................................. 600/529

* cited by examiner

Primary Examiner—Nicholas D. Lucchesi
(74) Attorney, Agent, or Firm—Bereskin & Parr

(57) ABSTRACT

A curing light for dental filling materials is used in combination with a light guide that bears a unique identifying code. A code reader in the nose cone of the curing light compares the code on the light guide with stored codes. If the code is a new code, a timer is started and provides a time out signal after expiry of a predetermined time representing the working time of the light guide. The time out signal may deactivate the light so that it cannot be used again until a new tip is inserted.

9 Claims, 5 Drawing Sheets

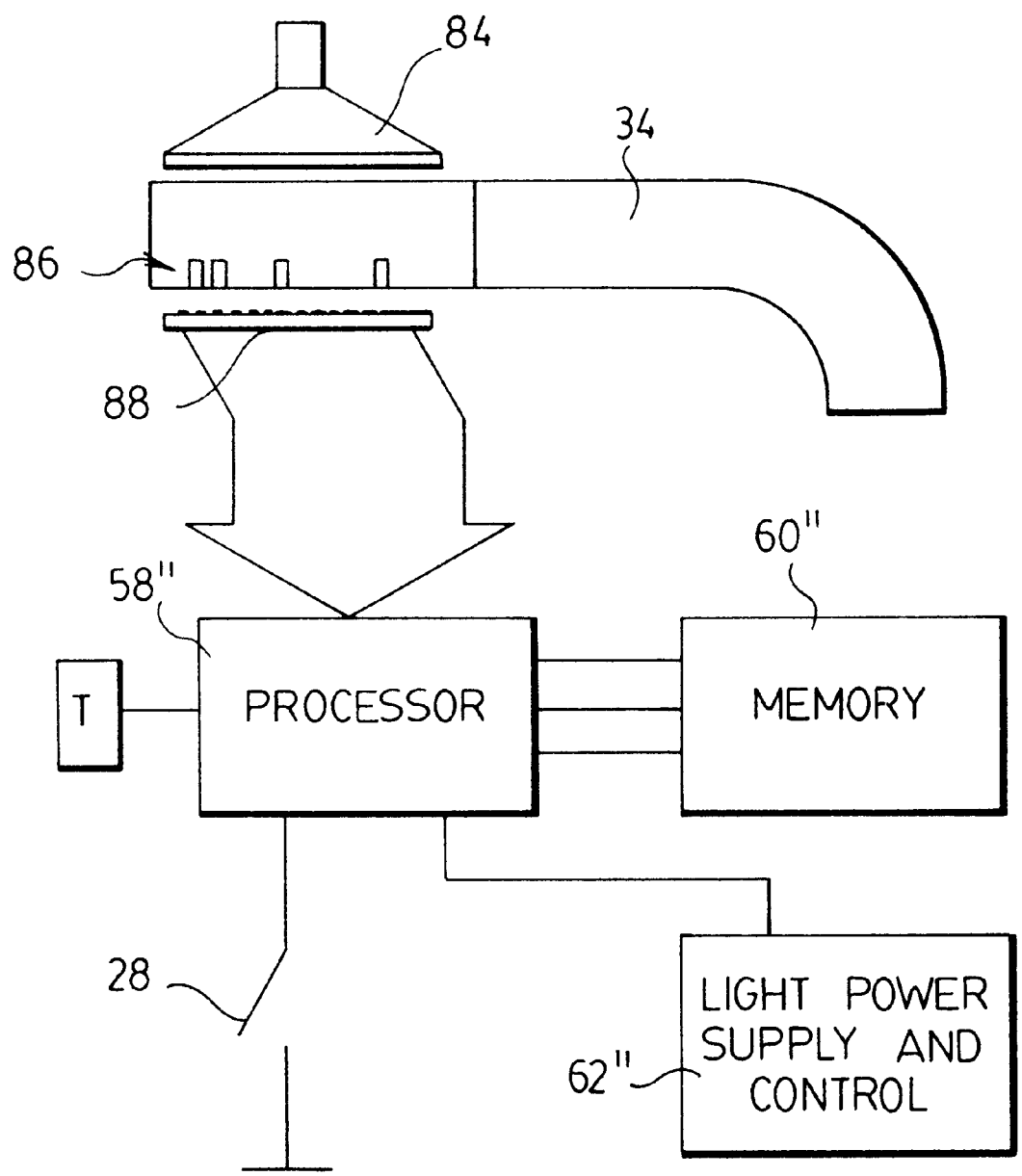

MEDICAL DEVICE WITH TIME-OUT FEATURE

FIELD OF THE INVENTION

This invention relates generally to medical devices (including dental devices) of the type that include a patient-contact element that should be replaced at intervals.

BACKGROUND OF THE INVENTION

The invention has been devised primarily in the context of light curing guns for dental filling materials. An example of a gun of this type is disclosed in U.S. Pat. No. 5,803,729 (Tsimerman). In a typical light curing gun, light from a halogen bulb is reflected into a light guide, by which the light is directed onto the dental filling material to be cured. Since the light guide necessarily enters the mouth of the patient, it should be sterile. If the same light guide is used repeatedly, it should be sterilized or replaced between patients. As disclosed in the Tsimerman patent, the light guide is simply push-fitted into a sleeve that provides a receptacle in the nose cone of the gun. Accordingly, it is quite a simple matter to change the light guide.

Traditionally, fibre optic light guides have been used. Performance of the curing light is significantly affected by the degree of transmission of light through a fibre optic light guide. Sterilization of these light guides results in decreased light transmission. In addition, cleaning and maintenance of fibre optic light guides is time consuming and costly.

Plastic disposable light guides were introduced several years ago. Re-use of non-sterilized light guides, which might even occur accidentally, would be hazardous to both the patient and to the dentist in view of the strict infection control guidelines of recent years. However, plastic light guides do not respond well to sterilization processes that employ heat. Lengthy immersion in cold sterilizing solutions causes cracking and yellowing of the plastic.

Similar considerations apply in relation to other medical devices that have replaceable patient-contact elements. Examples are electric toothbrushes where the toothbrush head typically is replaceable and dental irrigation devices having water nozzles. Sterility may not be as critical in these cases in the sense that there would normally be only a single user for one brush head. Nevertheless, toothbrush heads and nozzles do degrade with time and should periodically be replaced. Some types of medical syringe have dispensing tips that require replacement from time to time.

An object of the present invention is to provide means for at least indicating to the user of the device that the patient contact element should be replaced.

SUMMARY OF THE INVENTION

Accordingly, the invention provides the combination of a medical device and a patient contact element for use with the device, in which the device includes a receptacle for replaceably receiving the element. The element is encoded with a unique identifying code and the device includes a reader for the code. A data processor compares the code with codes previously read by that reader and provides a signal if the code is a new code. The device also includes a timer which is responsive to that signal and which provides a time-out signal after expiry of a predetermined time period selected as appropriate for replacement of the patient contact element. The time-out signal activates means for indicating to a user that the element should be replaced.

Preferably, this indication is provided by disabling the device until the patient contact element has been replaced. In the case of a device that is power operated, such as the light curing gun, the gun can be disabled simply by interrupting the power supply to the light. The dentist would then be forced to replace the patient contact element (light guide) before the light gun could be used again. In other cases, it may be sufficient to provide the user with a visual and/or audible signal to indicate that the patient contact element should be replaced.

The encoding/reading functions required pursuant to the invention can be provided using conventional technology such as bar coding or microchip coding, for example, as is used in conjunction with credit and other cards. Similar technology is also used in anti-theft devices for motor vehicles where a specially encoded ignition key must be used before a vehicle can be started.

In the context of light curing guns, it is thought that bar coding may be the preferred approach. Each light guide (sometimes called a "tip") can be encoded using code tape or a surface applied code. The nose cone of the light gun then incorporates a bar code reader. When the data processor receives a code from the reader, it compares this code with codes stored in its memory. If the code is a "new code", the processor sends a signal to trigger the timer which then starts to count down the working time of the tip (a constant stored in the processor's memory). This may happen immediately or only after first light exposure through the light guide. After the working time has expired, the processor interrupts the power supply to the light gun, effectively preventing further use of the gun. The only way in which the light gun can be re-activated is to insert a new light guide, which will send a new code to the processor.

Typically, the processor is a microprocessor incorporated in the light gun itself, or in an ancillary unit (e.g. housing power supply and control equipment). The microprocessor will include timer means. Reasonable memory capability will allow up to 1,000,000 codes to be stored. Once the memory is full, the next tip inserted will erase and reset the memory. The code may comprise 24–33 binary digits which will provide for 16 million–one billion codes.

BRIEF DESCRIPTION OF DRAWINGS

In order that the invention may be more clearly understood, reference will now be made to the accompanying drawings which schematically illustrate a number of preferred embodiments of the invention by way of example, in the context of a light curing gun for dental filling materials.

In the drawings:

FIGS. 6 and 7 are views similar to FIG. 2 illustrating further alternative forms of bar code reader.

DESCRIPTION OF PREFERRED EMBODIMENTS

Figure 1:
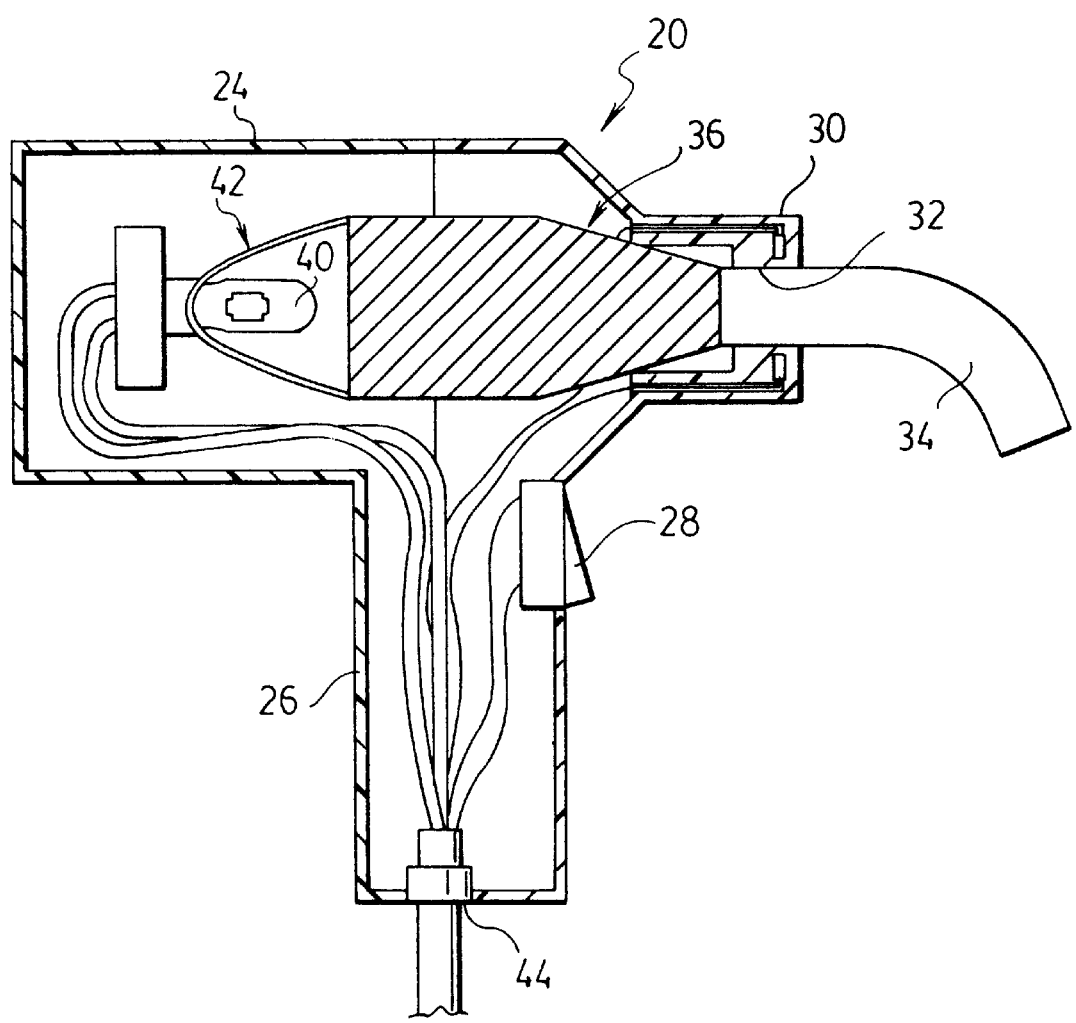
FIG. 1 is a schematic sectional view through a light curing gun of the general form disclosed in the Tsimerman '729 patent referred to previously.

Referring first to FIG. 1, a light curing gun is generally denoted by reference numeral 20 and includes a housing 22 that defines a main body portion 24 and a hand grip portion 26 that includes a trigger 28. At the forward end of the main body portion 24 is a nose cone 30 that provides a receptacle 32 for a light guide 34. The light guide 34 is simply inserted into the receptacle 32 and is readily replaceable or interchangeable with light guides of other configurations.

The receptacle 32 positions the light guide at the output end of a light collection system 36 having at its input end a light bulb 40 that is mounted within a reflector 42.

A conduit 44 for electrical cables and cooling fluid piping extends from the bottom end of the handle of the gun to an external unit (not shown) that houses power supplies and other ancillary components.

It should at this point be understood that the preceding description is provided by way of general background, for the purpose of indicating a typical environment in which the invention may be used. While the invention is not limited in its application to light curing guns, reference may be made to the Tsimerman '729 patent for specific details of one form of curing gun to which the invention may be applied.

Figure 2:
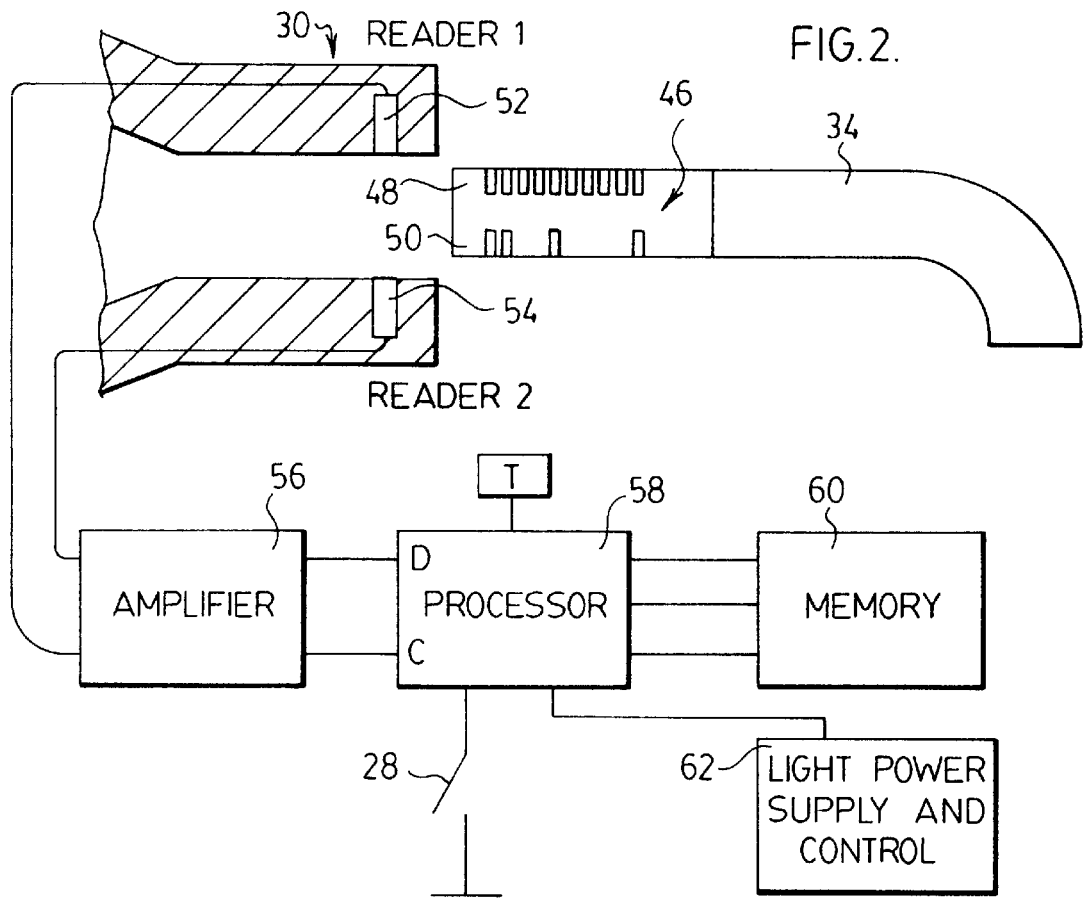
FIG. 2 is a schematic illustration of the light guide (tip) of the gun of FIG. 1, in combination with a reflective bar code reader and associated circuitry.

FIG. 2 shows a portion of the nose cone 30 of the gun of FIG. 1, with a light guide 34 in an exploded position outwardly of the nose cone. In accordance with the invention, the light guide 34 is provided with a unique identifying code, which in this embodiment comprises bar coding generally indicated at 46. The code itself is shown in more detail in FIG. 3. Essentially, there are two strips or tracks of bar codes at locations that are angularly spaced 90° about the light guide. The two strips of codes are denoted respectively 48 and 50 and the nose cone 30 includes readers 52 and 54 for the respective strips. For convenience of illustration, the readers are shown at diametrally opposed locations though in practice they will be angularly spaced at 90° from one another to match the code strips 48, 50. In an alternative embodiment, the readers could be external to the nose cone. The two readers 52 and 54 are connected in electrical circuitry that includes an amplifier 56, a signal processor 58, a memory 60 and a unit 62 that supplies power to and controls the light 40 of the curing gun. The trigger switch 28 of the curing gun is diagrammatically represented in FIG. 2, also at 28.

Figure 3:
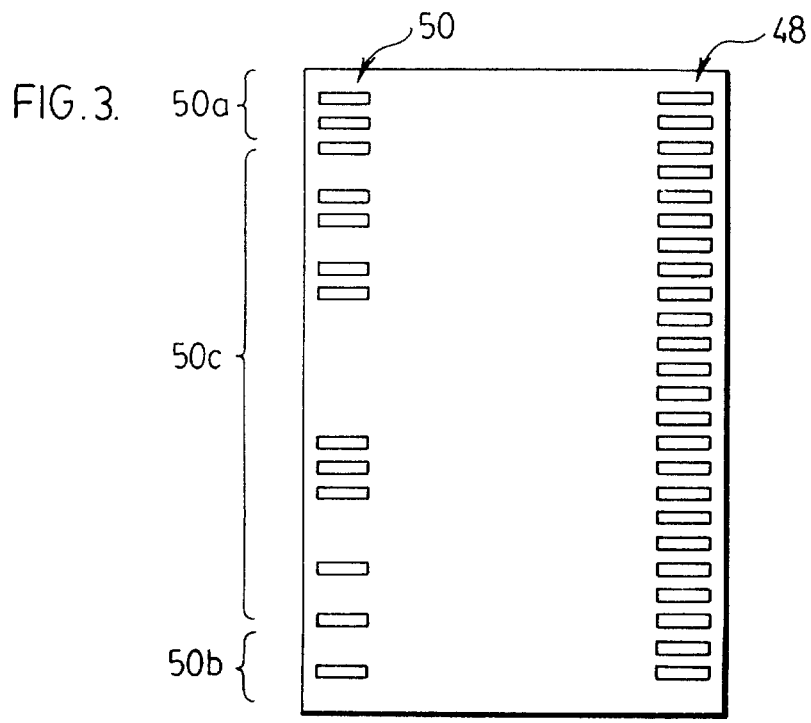
FIG. 3 is a developed view of a typical bar code as applied to a light guide.

Referring now to FIG. 3, code strip 50 is a unique identifying code specific to the particular tip. Code strip 48 provides a "count" for verifying full insertion of the light guide into a nose cone, and then initiates reading of code strip 50. Thus, code strip 48 comprises a defined number of bars that are in effect "counted" by the reader 52 (reader 1) when the light guide is inserted into the nose cone. Code strip 50 is read by reader 54 (reader 2) and includes a series of bars 50a at the leading end of the tip (the end that is inserted into the cone) representing a "start byte" and a series of bars 50c between the start byte and the stop byte comprising the actual unique identifying code.

Reverting to FIG. 2, when the light guide or tip 34 is being inserted into the nose cone 30, reader 1 (52) reads the code strip 48. A series of pulses is generated at a first port (denoted C of microprocessor 58). At the same time, the value represented by the synchronizing pulses (code strip 48) is written into the memory 60. The processor 58 checks the number of synchronizing pulses from code strip 48 to verify complete insertion of the tip. The processor also checks the start byte represented by the bars 50a and the stop byte represented by the bar 50b and the code represented by the bars 50c. The start and stop bytes have different values so that the process can distinguish between insert and removal of the tip.

The processor 58 compares the code represented by the bars 50c with codes stored in memory 60. If the code is a "new code" the processor 58 provides a signal to a timer "T" which begins to count down the working time of the tip (a constant stored in the memory 60). The working time is selected to be representative of a typical maximum time for which the tip should be used (e.g. one hour). After the working time has expired, the microprocessor sends a signal to the control unit 62 which interrupts the power supply to the bulb 40 of the curing gun.

At this stage, the gun can be reactivated only by inserting a new light guide having a new code.

Alternatively, the timer may not be activated until trigger 28 is squeezed so that only actual working time is recorded.

In the drawings, the circuitry including the microprocessor 58 has been shown diagrammatically only, since it would be well within the competence of a person skilled in the art of bar code readers to design circuitry that would provide the functions required pursuant to the present invention. Typically, the memory 60 will allow up to 1,000,000 codes to be stored. Once the memory is full, insertion of the next tip will cause the memory to be erased so that 1,000,000 can be stored again. The code may be made up of 24–33 binary digits which will allow 16 million one billion codes.

The timer T typically provides for a series of "parallel" timing registers so that different time values can be stored for different codes. If a tip is removed from the curing gun before its working time has expired, the remainder of the working time will be stored in the memory 60. If that tip is then reinserted into the curing gun, the bar code reader will recognize an old code and will respond to the value of the time remaining that is associated with that code. In other words, the timer will keep track of the working time of a particular tip even if that tip is removed from the gun and later reinserted.

This allows a dentist to exchange tips during a procedure that may require different tips to be used on the same patient, while at the same time keeping track of the overall working time of each tip and the amount of that time that has been used.

In this context, it should be noted that the representation in the drawings of the timer means of the invention as a separate timer is for illustrative purposes only. In practice, the timer means may be represented by individual registers in memory 60. For example, when the microprocessor 58 reads a code, it may assign a memory register to that code, in which is stored the pre-determined working time for the light guide. Different registers in the memory would store working times corresponding to other codes representing different light guides.

To prevent lateral light leakage through the tip being interpreted as a code, the microprocessor 58 will interrupt the code reading process if the trigger 28 of the light gun is activated.

Though not specifically shown in the drawings, mechanical guide means may be provided to assure correct rotational positioning of the light guide with respect to the nose cone, and consequent positioning of the code strips 48 and 50 with respect to the associated readers 52 and 54. In practice, this may not be absolutely necessary since the shape of the light guide will be indicative of the position it should adopt in the gun. Also, the bar codes are of significant lateral extent so that the precise rotational positioning is not essential.

As shown in FIG. 2, the readers 52 and 54 are reflective code readers. In other words, each reader is itself an emitter and receiver of light and the light is reflected from the bar codes.

Figure 4:
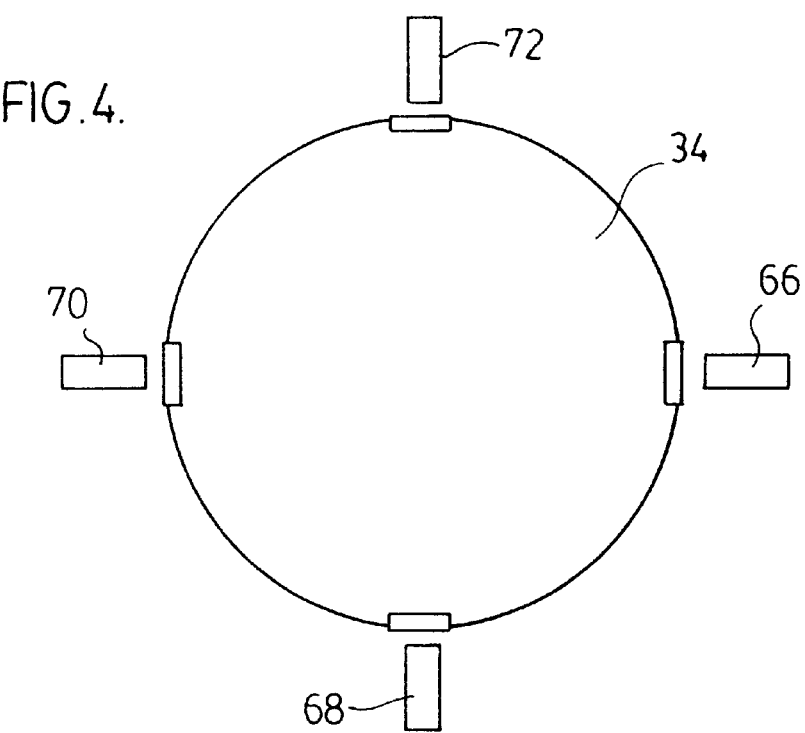
FIG. 4 is an end elevational view of the bar code reader of FIG. 2.

FIG. 4 shows an alternative embodiment in which multiple reflective code readers are used. The code carried by the light guide is divided into three consecutive fragments, each of which is read by one of three readers. For example, as shown in FIG. 4, a so-called "major nibble" reader is indicated at 66 and reads a first fragment, an intermediate nibble reader is indicated at 68 and reads a second code fragment and a minor nibble reader is indicated at 70 and reads a third code fragment. A synchrotrack reader is indicated at 72 and is essentially the same as the reader 52 of FIG. 2. In operation, each of the three readers 66, 68 and 70 reads its corresponding fragment of code. The processor 58 then amalgamates the information from the individual readers.

Figure 5:
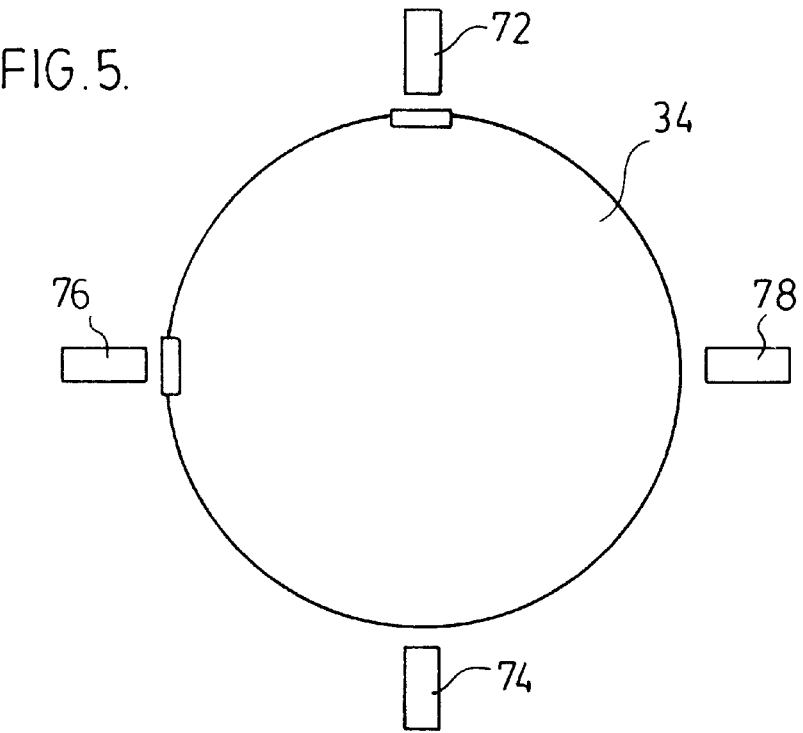
FIG. 5 is a view similar to FIG. 3 showing an alternative form of reader.

FIG. 5 shows an embodiment in which transmittive readers are used. In the case, a synchrotrack reader (for track 48) is indicated at 72 and comprises a photodiode that is illuminated by a corresponding illuminator 74 at a diametrally opposed location around the nose cone. Similarly, a photodiode code reader and a corresponding illuminator are indicated at 77 and 78 respectively for reading the code strip 50. Generally speaking, transmittive readers such as shown in FIG. 5 have the advantage of lower cost as compared with reflective readers.

Figure 6:
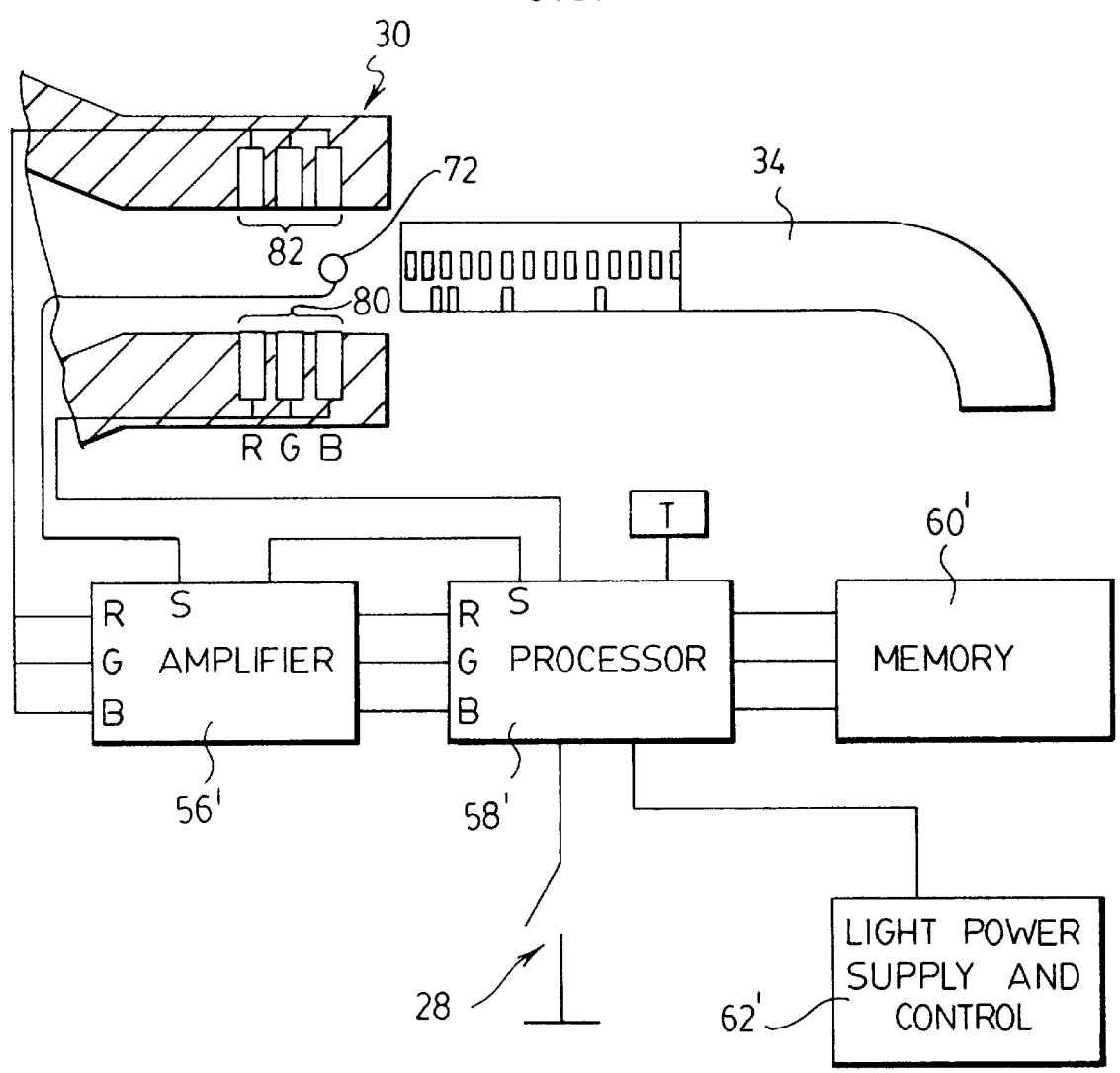

FIG. 6 is a view similar to FIG. 2 illustrating the use of transmittive code readers with additional colour coding. In this case, the reader for the synchrotrack 48 is the same as shown in FIG. 5, namely a photodiode reader 72 and a corresponding illuminator arranged as shown in FIG. 5 (illuminator not shown in FIG. 6).

Where colour coding is used, the single code reader 76 and code illuminator 78 of FIG. 5 is replaced by a series of illuminators 80 and a corresponding series of photodiodes 82 as shown in FIG. 6. The illuminators 80 emit light, respectively, in the red, green and blue portions of the spectrum and are denoted as R, G, and B. The electrical circuitry associated with the readers is essentially the same as shown in FIG. 2 except in that the amplifier (denoted 56') and the processor (denoted 58') are designed to deal with signals from the three photodiodes 82.

Addition of colour coding as in the embodiment of FIG. 6 has the advantage that it decreases demands on the dimensional accuracy of the codes.

Finally, FIG. 7 illustrates an embodiment of the invention in which parallel code readers are used. This type of reader has the advantage of economy and simplified programming, and avoids the need for a synchrotrack (track 48 referred to previously). In the embodiment of FIG. 7, a single illuminator 84 is provided for a code 86 carried by the tip. A corresponding photodiode array 88 is provided at a diametrally opposite location to the illuminator for responding to the code. Each diode in the array provides a signal to a processor 58" having associated memory 60" and light, power supply and control unit 62".

It will be appreciated from the foregoing that, within the broad scope of the invention, different techniques can be used for coding the individual light guides and reading the codes. Some examples have been shown specifically and other will be apparent to a person skilled in the art. As noted previously, another possibility is to use micro-chip coding such as is used in conjunction with credit and other cards or in anti-theft devices for motor vehicles.

Also as noted previously, while the invention has been described in the context of a light curing gun for dental materials, there is no limitation in this respect. The invention may be applied to other medical devices having patient contact elements that should be replaced from time to time. Generally, the invention aims to indicate to the user of such a device that the patient contact element should be replaced. This indication may take the form of action to actually disable the device, or merely an indication such as a visual or audible signal.

I claim:

1. The combination of a medical device and a patient-contact element for use with the device, the device including a receptacle for replaceably receiving said patient-contact element;
    wherein the element is encoded with an unique identifying code and the device includes: a reader for said code; a data processor for comparing said code with codes previously read by that reader and providing a signal if the code is a new code; timer means responsive to said signal and adapted to provide a time-out signal after expiry of a predetermined time period selected as appropriate to replacement of said patient contact element; and means responsive to the time-out signal for indicating to a user of the device that the element should be replaced.

2. The combination claimed in claim 1, further comprising means responsive to said time out signal for de-activating the medical device until a new patient contact element is in place in said receptacle.

3. The combination as claimed in claim 2, wherein the medical device is a curing light for dental filling materials, including a light source, and the patient-contact element is a light guide, and wherein said means responsive to the time out signal is arranged to de-activate the light source.

4. The combination as claimed in claim 1, wherein said unique identifying code is a bar code.

5. The combination as claimed in claim 4, wherein the bar code comprises first and second code strips and respective readers for said strips, said first code strip comprising a defined number of bars which are counted by the associated reader, for providing an indication that the patient contact element has been fully inserted into the receptacle and initiating reading of the identifying code, and wherein the second code strip comprises a start byte, a stop byte, and an intervening code which uniquely identifies the patient contact element.

6. The combination as claimed in claim 1, wherein said timer means is adapted to record the used working time of a plurality of different patient contact elements, each having its own unique identifying code.

7. The combination as claimed in claim 1, wherein said code is a bar code and wherein said reader is selected from the group comprising a reflective code reader, a transmissive code reader and a parallel code reader.

8. For use in combination with a light guide bearing a unique identifying code, a curing light for dental filling materials including a receptacle for receiving said light guide; a reader for said code; a data processor for comparing said code with codes previously read by that reader and providing a signal if the code is a new code; timer means responsive to said signal and adapted to provide a time-out signal after expiry of a predetermined time period selected as appropriate to replacement of said light guide; and means responsive to said time-out signal for de-activating the light.

9. For use in combination with a curing light as claimed in claim 8, a light guide having an end portion for entry into said receptacle of the curing light, wherein said end portion of the light guide is provided with a bar code uniquely identifying said light guide.

* * * * *